(12) United States Patent
Shilov et al.

(10) Patent No.: US 11,181,511 B2
(45) Date of Patent: Nov. 23, 2021

(54) RAPID SCORING OF LC-MS/MS PEPTIDE DATA

(71) Applicant: DH Technologies Development Pte. Ltd., Singapore (SG)

(72) Inventors: Ignat V. Shilov, Palo Alto, CA (US); Stephen A. Tate, Barrie (CA)

(73) Assignee: DH Technologies Development Pte. Ltd., Singapore (SG)

( * ) Notice: Subject to any disclaimer, the term of this patent is extended or adjusted under 35 U.S.C. 154(b) by 312 days.

(21) Appl. No.: 15/753,580

(22) PCT Filed: Aug. 12, 2016

(86) PCT No.: PCT/IB2016/054867
§ 371 (c)(1),
(2) Date: Feb. 20, 2018

(87) PCT Pub. No.: WO2017/033087
PCT Pub. Date: Mar. 2, 2017

(65) Prior Publication Data
US 2020/0217829 A1  Jul. 9, 2020

Related U.S. Application Data

(60) Provisional application No. 62/210,695, filed on Aug. 27, 2015.

(51) Int. Cl.
*G01N 30/86* (2006.01)
*G01N 30/72* (2006.01)
(Continued)

(52) U.S. Cl.
CPC ..... *G01N 30/8655* (2013.01); *G01N 30/7233* (2013.01); *G06F 17/16* (2013.01);
(Continued)

(58) Field of Classification Search
CPC .. H01J 49/0045; H01J 49/34; G01N 30/7233; G01N 2030/027; G01N 30/8655; G06F 17/16; G06F 17/18
See application file for complete search history.

(56) References Cited

U.S. PATENT DOCUMENTS 9,377,469 B2 * 6/2016 Louette .............. G01N 30/8675
2005/0288872 A1 12/2005 Old et al.
(Continued)

FOREIGN PATENT DOCUMENTS

WO     2014195783 A1   12/2014

OTHER PUBLICATIONS

International Search Report and Written Opinion for PCT/IB2016/054867 dated Dec. 28, 2016.

*Primary Examiner* — Elias Desta
(74) *Attorney, Agent, or Firm* — John R. Kasha; Kelly L. Kasha; Kasha Law LLC

(57) ABSTRACT

A plurality of product ion spectra measured over plurality of cycles for each precursor ion mass selection window of two or more precursor ion mass selection windows are received from a tandem mass spectrometer. A product ion extracted ion chroatograms (XIC) is calculated for each precursor ion mass selection window of the two or more precursor ion mass selection windows from the plurality of product ion spectra for each precursor ion mass selection window. Two or more product ion XICs are produced. A two-dimensional binary bit matrix is generated to represent each product ion XIC of the two or more product ion XICs. For each XIC of the two or more product ion XICs, the binary bit matrix is separately initialized with binary values calculated from each XIC and the initialized binary bit matrix is compared with stored information about known compounds to identify known compounds of each XIC.

15 Claims, 12 Drawing Sheets

(51) Int. Cl.
  *G06F 17/16* (2006.01)
  *G06F 17/18* (2006.01)
  *H01J 49/00* (2006.01)
  *H01J 49/34* (2006.01)
  *G01N 30/02* (2006.01)

(52) U.S. Cl.
  CPC .......... *G06F 17/18* (2013.01); *H01J 49/0045* (2013.01); *H01J 49/34* (2013.01); *G01N 2030/027* (2013.01)

(56) References Cited

U.S. PATENT DOCUMENTS

| | | |
|---|---|---|
| 2009/0090857 A1 | 4/2009 | Sigman et al. |
| 2012/0049058 A1 | 3/2012 | Grothe, Jr. |
| 2015/0144778 A1 | 5/2015 | Bonner et al. |
| 2018/0240658 A1* | 8/2018 | Cox .................... H01J 49/0031 |

* cited by examiner

RAPID SCORING OF LC-MS/MS PEPTIDE DATA

CROSS REFERENCE TO RELATED APPLICATION

This application claims the benefit of U.S. Provisional Patent Application Ser. No. 62/210,695, filed Aug. 27, 2015, the content of which is incorporated by reference herein in its entirety.

INTRODUCTION

Various embodiments relate generally to mass spectrometry. More particularly various embodiments relate to systems and methods for matching fragments of theoretical peptides to traces or extracted ion chromatograms (XICs) experimentally measured from a sample.

A common problem in proteomics is determining the identity of the proteins present in a sample. Typically, proteins are identified in a sample using a two-step tandem mass spectrometry process. In the first step, experimental data is obtained. The proteins in the sample are digested using an enzyme such a trypsin, producing one or more peptides for each protein. Note that a peptide, as used herein, is a digested portion of a protein. Some proteins can be digested intact, so a peptide can also be the entire protein. However, in most cases peptides are digested portions of proteins.

The peptides digested from proteins are then separated from the sample over time using a sample introduction device or separation device. The separated peptides are then ionized using an ion source. The ionized peptides, or peptide precursor ions, are selected by mass-to-charge ratio (m/z), the selected precursor ions are fragmented, and the resulting product ions are mass analyzed using a tandem mass spectrometer. The result of the first step is a collection of one or more product ion mass spectra measured at one or more different times.

In the second step, computer generated information about known proteins expected to be in the experimental sample is compared to the experimental data. The known proteins are obtained from a database, and are computationally digested using the same enzyme used in the tandem mass spectrometry experiment, producing one or more theoretical peptides for each known protein. The theoretical peptides are computationally selected and fragmented, producing theoretical product ions for each known protein. The resulting theoretical product ions are then compared to each of the one or more measured product ion mass spectra at each of the one or more different times. Typically, known proteins are scored based on how well their theoretical product ions match the one or more measured product ion mass spectra. The proteins in the sample are then identified from the highest scoring known proteins.

Unfortunately, however, this method of identifying peptides in a sample quickly becomes computationally expensive as the number of different product ions in each experimental product ion spectrum increases. In other words, as the number of different product ions in each experimental product ion spectrum increases so does the number of comparisons with product ions of theoretical peptides.

This increased computational expense is particularly a problem for SWATH acquisition. SWATH acquisition is a tandem mass spectrometry method in which large precursor ion mass selection windows are stepped across an entire precursor ion m/z range. Each large precursor ion mass selection window can include a large number of different precursor ions, which results in product ion spectra that each includes a large number of different product ions. In addition, because multiple precursor ions are fragmented in the same precursor ion mass selection window, it is difficult to determine the precursor ion that produced each product ion.

In general, tandem mass spectrometry, or MS/MS, is a well-known technique for analyzing compounds. As described above, tandem mass spectrometry involves ionization of one or more compounds from a sample, selection of one or more precursor ions of the one or more compounds, fragmentation of the one or more precursor ions into product ions, and mass analysis of the product ions.

Tandem mass spectrometry can provide both qualitative and quantitative information. The product ion spectrum can be used to identify a molecule of interest. The intensity of one or more product ions can be used to quantitate the amount of the compound present in a sample.

A large number of different types of experimental methods or workflows can be performed using a tandem mass spectrometer. Three broad categories of these workflows are, targeted acquisition, information dependent acquisition (IDA) or data dependent acquisition (DDA), and DIA.

In a targeted acquisition method, one or more transitions of a peptide precursor ion to a product ion are predefined for one or more proteins. As a sample is being introduced into the tandem mass spectrometer, the one or more transitions are interrogated during each time period or cycle of a plurality of time periods or cycles. In other words, the mass spectrometer selects and fragment the peptide precursor ion of each transition and performs a targeted mass analysis for the product ion of the transition. As a result, a mass spectrum is produced for each transition. Targeted acquisition methods include, but are not limited to, multiple reaction monitoring (MRM) and selected reaction monitoring (SRM).

IDA is a flexible tandem mass spectrometry method in which a user can specify criteria for performing targeted or untargeted mass analysis of product ions while a sample is being introduced into the tandem mass spectrometer. For example, in an IDA method a precursor ion or mass spectrometry (MS) survey scan is performed to generate a precursor ion peak list. The user can select criteria to filter the peak list for a subset of the precursor ions on the peak list. MS/MS is then performed on each precursor ion of the subset of precursor ions. A product ion spectrum is produced for each precursor ion. MS/MS is repeatedly performed on the precursor ions of the subset of precursor ions as the sample is being introduced into the tandem mass spectrometer.

In proteomics and many other sample types, however, the complexity and dynamic range of compounds are very large. This poses challenges for traditional targeted and IDA methods, requiring very high-speed MS/MS acquisition to deeply interrogate the sample in order to both identify and quantify a broad range of analytes.

As a result, DIA methods have been used to increase the reproducibility and comprehensiveness of data collection from complex samples. DIA methods can also be called non-specific fragmentation methods. In a traditional DIA method, the actions of the tandem mass spectrometer are not varied among MS/MS scans based on data acquired in a previous precursor ion or product ion scan. Instead, a precursor ion mass range is selected. A precursor ion mass selection window is then stepped across the precursor ion mass range. All precursor ions in the precursor ion mass selection window are fragmented and all of the product ions of all of the precursor ions in the precursor ion mass selection window are mass analyzed.

The precursor ion mass selection window used to scan the mass range can be very narrow so that the likelihood of multiple precursors within the window is small. This type of DIA method is called, for example, MS/MS$^{ALL}$. In an MS/MS$^{ALL}$ method, a precursor ion mass selection window of about 1 amu is scanned or stepped across an entire mass range. A product ion spectrum is produced for each 1 amu precursor mass window. A product ion spectrum for the entire precursor ion mass range is produced by combining the product ion spectra for each mass selection window. The time it takes to analyze or scan the entire mass range once is referred to as one scan cycle. Scanning a narrow precursor ion mass selection window across a wide precursor ion mass range during each cycle, however, is not practical for some instruments and experiments.

As a result, a larger precursor ion mass selection window, or selection window with a greater width, is stepped across the entire precursor mass range. This type of DIA method is called, for example, SWATH acquisition. In SWATH acquisition the precursor ion mass selection window stepped across the precursor mass range in each cycle may have a width of 5-25 amu, or even larger. Like the MS/MS$^{ALL}$ method, all the precursor ions in each precursor ion mass selection window are fragmented, and all of the product ions of all of the precursor ions in each mass isolation window are mass analyzed. However, because a wider precursor ion mass selection window is used, the cycle time can be significantly reduced in comparison to the cycle time of the MS/MS$^{ALL}$ method.

U.S. Pat. No. 8,809,770 describes how SWATH acquisition can be used to provide quantitative and qualitative information about the precursor ions of compounds of interest. In particular, the product ions found from fragmenting a precursor ion mass selection window are compared to a database of known product ions of compounds of interest. In addition, ion traces or extracted ion chromatograms (XICs) of the product ions found from fragmenting a precursor ion mass selection window are analyzed to provide quantitative and qualitative information.

As described above, however, identifying peptides in a sample analyzed using SWATH acquisition quickly becomes computationally expensive. This is because SWATH acquisition typically results in a large number of different product ions in each product ion spectrum. In other words, as the number of different product ions in each product ion spectrum increases so does the number of required comparisons with product ions of theoretical peptides.

SUMMARY

A system is disclosed for representing product ion extracted ion chromatograms (XICs) obtained from a tandem mass spectrometry data independent acquisition (DIA) experiment as a binary bit matrix and using the binary bit matrix to identify compounds by comparing the binary bit matrix to stored information about known compounds. The system includes a sample introduction device, an ion source, a tandem mass spectrometer, and a processor.

The sample introduction device introduces one or more compounds of a sample over time. The ion source is configured to receive the one or more compounds from the sample introduction device and ionize the one or more compounds, producing an ion beam of precursor ions. The tandem mass spectrometer is configured to receive the ion beam of precursor ions that divides a mass-to-charge ratio (m/z) range of the ion beam into two or more precursor ion mass selection windows and selects and fragments the two or more precursor ion mass selection windows during each cycle of a plurality of cycles, producing a plurality of product ion spectra for each precursor ion mass selection window of the two or more precursor ion mass selection windows.

The processor receives a plurality of product ion spectra for each precursor ion mass selection window of the two or more precursor ion mass selection windows. The processor calculates a product ion XIC for each precursor ion mass selection window of the two or more precursor ion mass selection windows from the plurality of product ion spectra for each precursor ion mass selection window, producing two or more product ion XICs.

The processor generates a two-dimensional binary bit matrix to represent each product ion XIC of the two or more product ion XICs. A first dimension of the binary bit matrix represents a mass of a product ion XIC. A second dimension of the binary bit matrix represents a cycle time of the product ion XIC. Each element of the binary bit matrix is a binary value that represents whether or not an intensity of a product ion XIC at each mass and cycle time is within a predetermined peak intensity threshold.

For each XIC of the two or more product ion XICs, the processor separately initializes the binary bit matrix with binary values calculated from the each XIC. The processor compares the initialized binary bit matrix with stored information about known compounds to identify known compounds of the each XIC.

A method is disclosed for representing product ion XICs obtained from a tandem mass spectrometry DIA experiment as a binary bit matrix and using the binary bit matrix to identify compounds by comparing the binary bit matrix to stored information about known compounds.

A plurality of product ion spectra for each precursor ion mass selection window of two or more precursor ion mass selection windows are received from a tandem mass spectrometer using a processor. The plurality of product ion spectra is produced by the tandem mass spectrometer by dividing an m/z range of an ion beam into two or more precursor ion mass selection windows and selecting and fragmenting the two or more precursor ion mass selection windows during each cycle of a plurality of cycles. The ion beam is produced by an ion source that ionizes one or more compounds of a sample. The one or more compounds are produced by a sample introduction device that introduces one or more compounds of a sample to the ion source over time.

A product ion XIC is calculated for each precursor ion mass selection window of the two or more precursor ion mass selection windows from the plurality of product ion spectra for each precursor ion mass selection window using the processor. Two or more product ion XICs are produced.

A two-dimensional binary bit matrix is generated to represent each product ion XIC of the two or more product ion XICs using the processor. A first dimension of the binary bit matrix represents a mass of a product ion XIC. A second dimension of the binary bit matrix represents a cycle time of the product ion XIC. Each element of the binary bit matrix is a binary value that represents whether or not an intensity of a product ion XIC at each mass and cycle time is within a predetermined peak intensity threshold.

For each XIC of the two or more product ion XICs, the binary bit matrix is separately initialized with binary values calculated from the each XIC and the initialized binary bit matrix is compared with stored information about known compounds to identify known compounds of the each XIC using the processor.

A computer program product is disclosed that includes a non-transitory and tangible computer-readable storage medium whose contents include a program with instructions being executed on a processor so as to perform a method for representing product ion XICs obtained from a tandem mass spectrometry DIA experiment as a binary bit matrix and using the binary bit matrix to identify compounds by comparing the binary bit matrix to stored information about known compounds. In various embodiments, the method includes providing a system, wherein the system comprises one or more distinct software modules, and wherein the distinct software modules comprise an analysis module.

The analysis module receives receiving a plurality of product ion spectra for each precursor ion mass selection window of two or more precursor ion mass selection windows from a tandem mass spectrometer. The plurality of product ion spectra is produced by the tandem mass spectrometer by dividing m/z range of an ion beam into two or more precursor ion mass selection windows and selecting and fragmenting the two or more precursor ion mass selection windows during each cycle of a plurality of cycles. The ion beam is produced by an ion source that ionizes one or more compounds of a sample. The one or more compounds are produced by a sample introduction device that introduces one or more compounds of a sample to the ion source over time.

The analysis module calculates a product ion XIC for each precursor ion mass selection window of the two or more precursor ion mass selection windows from the plurality of product ion spectra for each precursor ion mass selection window, producing two or more product ion XICs. The analysis module generates a two-dimensional binary bit matrix to represent each product ion XIC of the two or more product ion XICs. A first dimension of the binary bit matrix represents a mass of a product ion XIC. A second dimension of the binary bit matrix represents a cycle time of the product ion XIC. Each element of the binary bit matrix is a binary value that represents whether or not an intensity of a product ion XIC at each mass and cycle time is within a predetermined peak intensity threshold.

For each XIC of the two or more product ion XICs, the analysis module separately initializes the binary bit matrix with binary values calculated from the each XIC. The analysis module then compares the initialized binary bit matrix with stored information about known compounds to identify known compounds of the each XIC.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
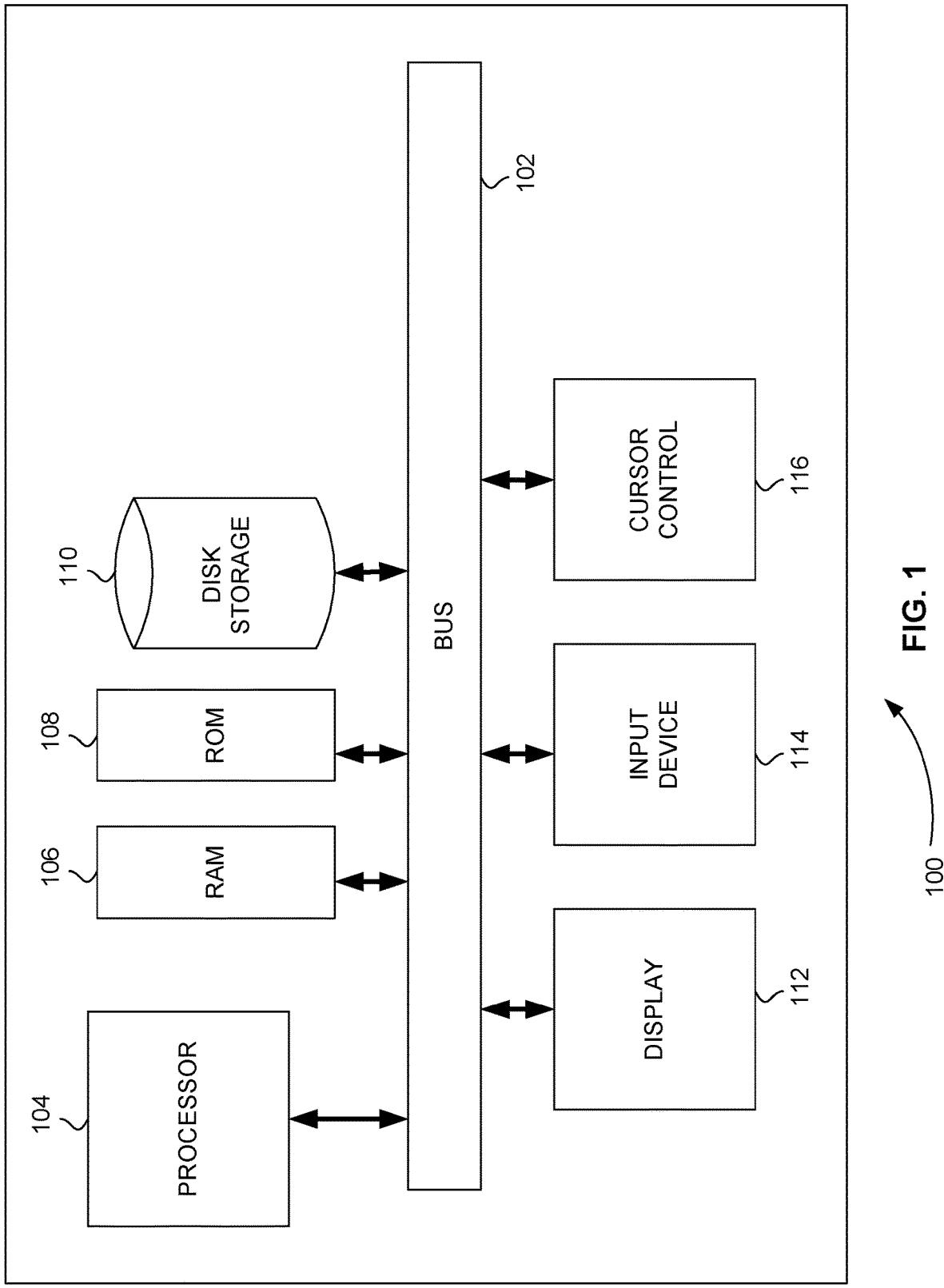
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Binary Bit Matrix Comparison

As described above, SWATH acquisition is a tandem mass spectrometry method well-suited for analyzing proteomic samples. However, identifying peptides in a sample analyzed using SWATH acquisition quickly becomes computationally expensive. This is because SWATH acquisition typically results in a large number of different product ions in each product ion spectrum. In other words, as the number of different product ions in each product ion spectrum increases, so does the number of required comparisons with product ions of theoretical peptides. To date, the mass spectrometry industry has been unable to obtain computationally efficient methods of comparing product ions of theoretical peptides with measured product ion spectra that each includes large numbers of different product ions.

In various embodiments, measured product ion data obtained over time for each precursor ion mass selection window of a SWATH acquisition is represented as a binary bit matrix. In order to compare theoretical peptides to the binary bit matrix of each precursor ion mass selection window, a submatrix of the binary bit matrix is obtained for each theoretical peptide. A comparison of each theoretical peptide with its corresponding submatrix is then performed. The comparison of each theoretical peptide with its corresponding submatrix is computationally efficient, because binary values can be compared very quickly using a digital computer.

More specifically, after a SWATH acquisition a series of steps are performed:

1. For each precursor ion mass selection window, an extracted ion chromatogram (XIC) is constructed from the product ions produced over time.

2. A binary bit matrix is generated to represent the product ion XIC of each precursor ion mass selection window.

3. For each product ion XIC of each precursor ion mass selection window, the binary bit matrix is separately initialized with binary values determined from the product ion XIC.

4. Stored information about known compounds is used to generate theoretical precursor ions.

5. Each theoretical precursor ion is matched to a corresponding precursor ion mass selection window, and for each theoretical precursor ion, theoretical product ions are generated.

6. For each theoretical precursor ion of each precursor ion mass selection window, the matching theoretical product ions are used to select bit masks from binary bit matrix initialized from the product ion XIC, and the bit masks are used to construct a submatrix of the binary bit matrix that represents the theoretical precursor ion.

7. The bits of each cycle time of each submatrix representing each theoretical precursor ion are efficiently counted producing a series of product ions scores or counts for a series of cycle times.

8. For each theoretical precursor ion of each precursor ion mass selection window, the series of product ions scores is used to calculate a probability of getting the scores randomly, and the theoretical precursor ion is identified as a compound of its precursor ion mass selection window based on the probability calculated.

1. Calculate XICs

Figure 2:
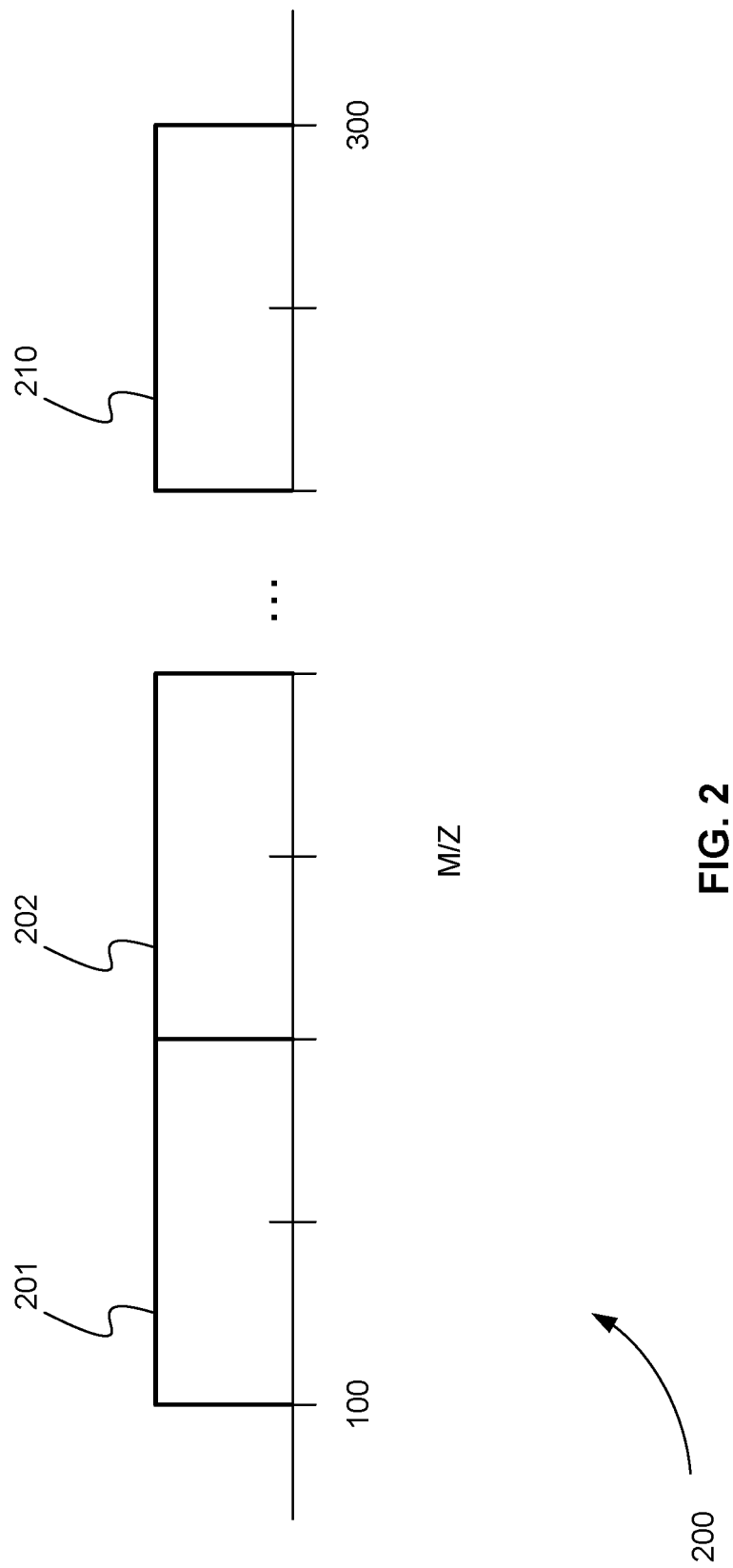
FIG. 2 is an exemplary diagram of a precursor ion mass-to-charge ratio (m/z) range that is divided into ten precursor ion mass selection windows for a data independent acquisition (DIA) workflow, in accordance with various embodiments.

FIG. 2 is an exemplary diagram 200 of a precursor ion mass-to-charge ratio (m/z) range that is divided into ten precursor ion mass selection windows for a data independent acquisition (DIA) workflow, in accordance with various embodiments. The m/z range shown in FIG. 2 is 200 m/z. Note that the terms "mass" and "m/z" are used interchangeably herein. Generally, mass spectrometry measurements are made in m/z and converted to mass by multiplying by the charge.

Each of the ten precursor ion mass selection or isolation windows spans or has a width of 20 m/z. Three of the ten precursor ion mass selection windows, windows 201, 202, and 210, are shown in FIG. 2. Precursor ion mass selection windows 201, 202, and 210 are shown as non-overlapping windows with the same width. In various embodiments, precursor ion mass selection windows can overlap and/or can have variable widths. U.S. patent application Ser. No. 14/401,032 describes using overlapping precursor ion mass selection windows in a single cycle of SWATH acquisition, for example. U.S. Pat. No. 8,809,772 describes using precursor ion mass selection windows with variable widths in a single cycle of SWATH acquisition using variable precursor ion mass selection windows in SWATH acquisition, for example. In a conventional SWATH acquisition, each of the ten precursor ion mass selection windows is selected and then fragmented, producing ten product ion spectra for the entire m/z range shown in FIG. 2.

FIG. 2 depicts non-variable and non-overlapping precursor ion mass selection windows used in a single cycle of an exemplary SWATH acquisition. A tandem mass spectrometer that can perform a SWATH acquisition method can further be coupled with a sample introduction device that separates one or more compounds from the sample over time, for example. A sample introduction device can introduce a sample to the tandem mass spectrometer using a technique that includes, but is not limited to, injection, liquid chromatography, gas chromatography, capillary electrophoresis, or ion mobility. The separated one or more compounds are ionized by an ion source, producing an ion beam of precursor ions of the one or more compounds that are selected and fragmented by the tandem mass spectrometer.

As a result, for each time step of a sample introduction of separated compounds, each of the ten precursor ion mass selection windows is selected and then fragmented, producing ten product ion spectra for the entire m/z range. In other words, each of the ten precursor ion mass selection windows is selected and then fragmented during each cycle of a plurality of cycles.

Figure 3:
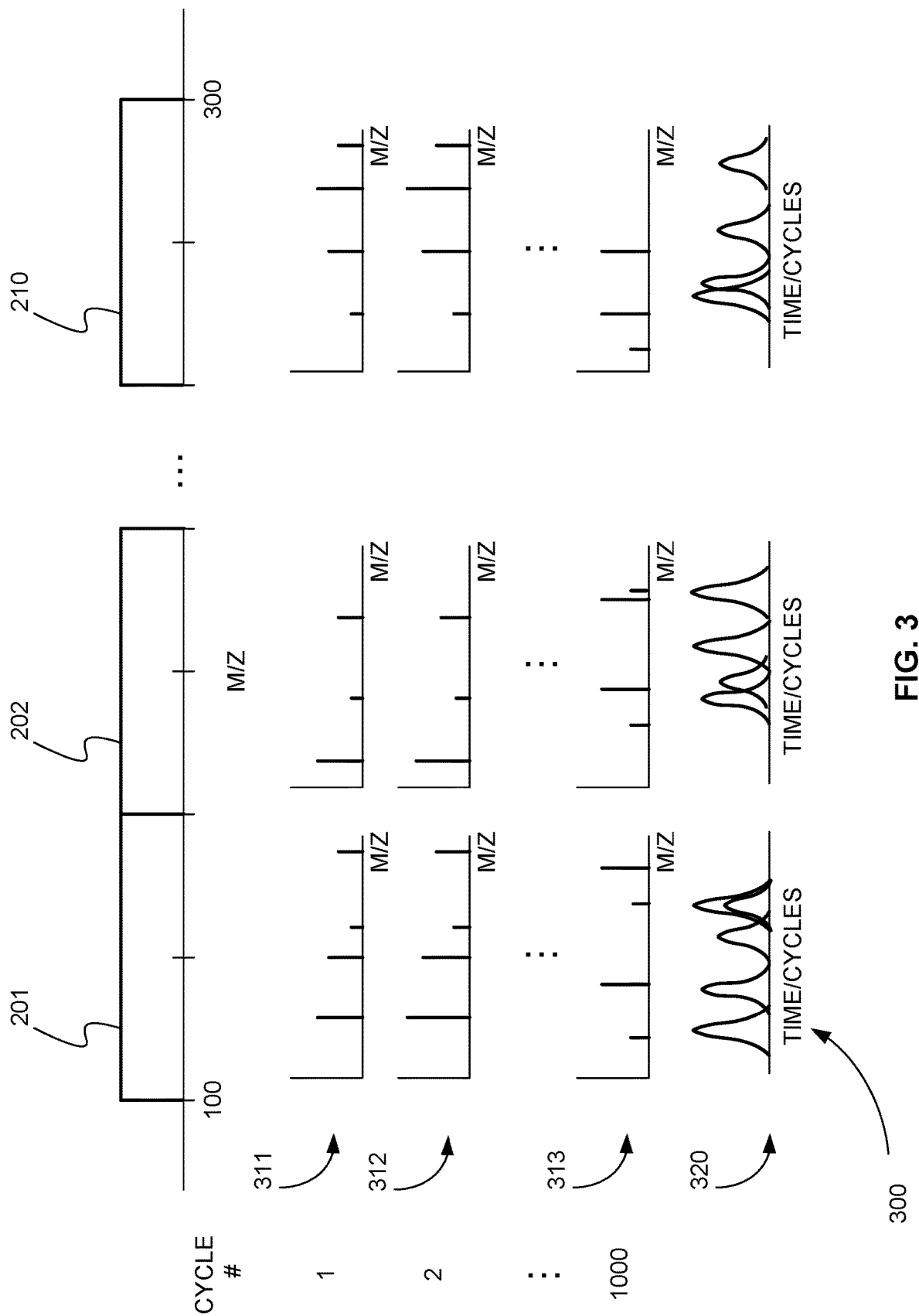
FIG. 3 is an exemplary diagram that graphically depicts the steps for obtaining product ion traces or extracted ion chromatograms (XICs) from each precursor ion mass selection window during each cycle of a DIA workflow, in accordance with various embodiments.

FIG. 3 is an exemplary diagram 300 that graphically depicts the steps for obtaining product ion traces or extracted ion chromatograms (XICs) from each precursor ion mass selection window during each cycle of a DIA workflow, in accordance with various embodiments. For example, ten precursor ion mass selection windows, represented by precursor ion mass selection windows 201, 202, and 210 in FIG. 3, are selected and fragmented during each cycle of a total of 1000 cycles.

During each cycle, a product ion spectrum is obtained for each precursor ion mass selection window. For example, product ion spectrum 311 is obtained by fragmenting precursor ion mass selection window 201 during cycle 1, product ion spectrum 312 is obtained by fragmenting precursor ion mass selection window 201 during cycle 2, and product ion spectrum 313 is obtained by fragmenting precursor ion mass selection window 201 during cycle 1000.

By plotting the intensities of the product ions in each product ion spectrum of each precursor ion mass selection window over time, XICs are obtained for each precursor ion mass selection window. For example, XIC 320 is calculated from the 1000 product ion spectra of precursor ion mass selection window 201. XIC 320 includes XIC peaks or traces for all of the product ions that are produced from fragmenting precursor ion mass selection window 201 during the 1000 cycles. Note that XICs can be plotted in terms of time or cycles.

XIC 320 is shown plotted in two dimensions in FIG. 3. However, each XIC of each precursor ion mass selection window is actually three-dimensional, because the different XIC peaks represent different m/z values.

Figure 4:
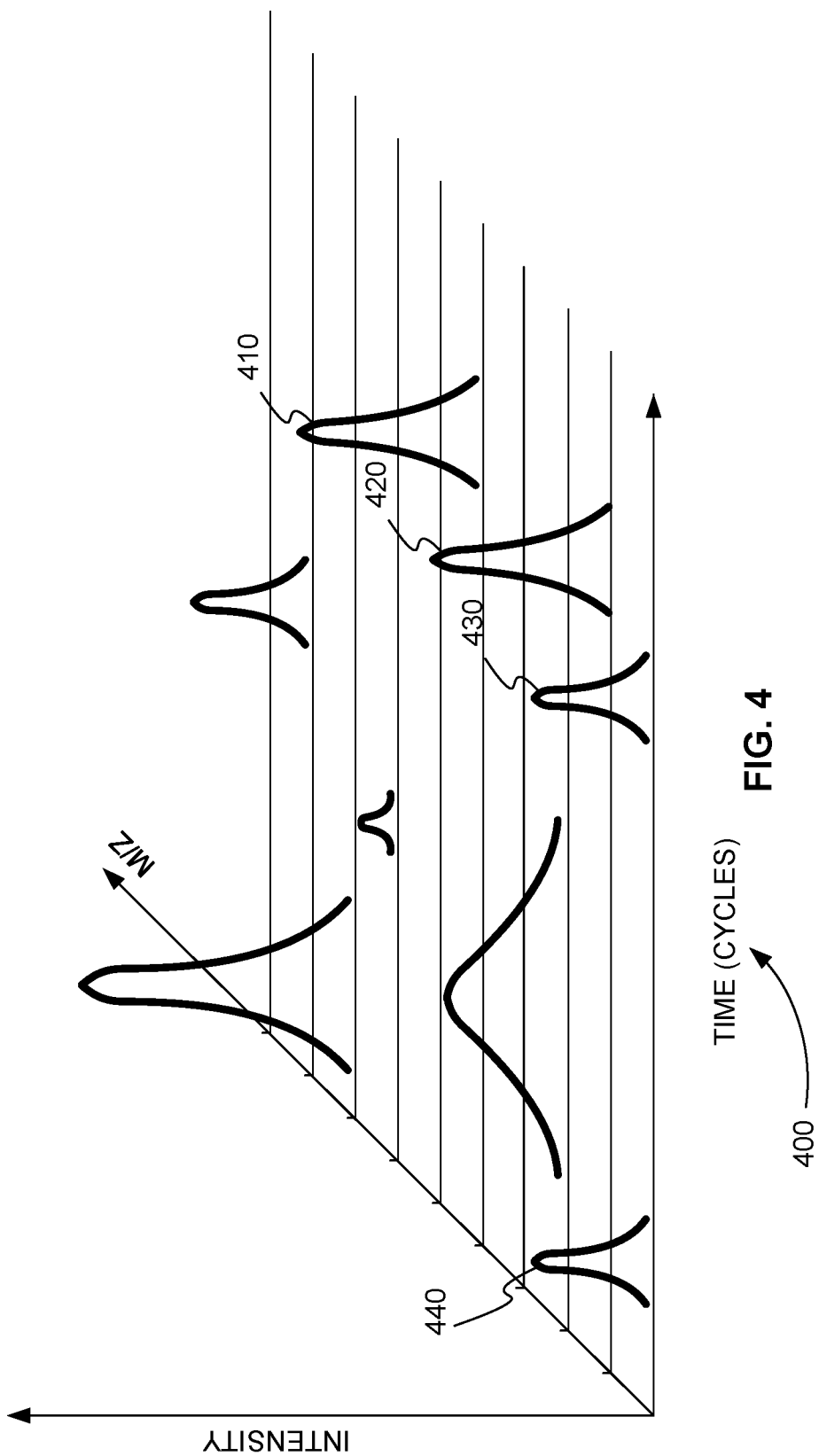
FIG. 4 is an exemplary diagram that shows the three-dimensionality of an XIC obtained for a precursor ion mass selection window over time, in accordance with various embodiments.

FIG. 4 is an exemplary diagram 400 that shows the three-dimensionality of an XIC obtained for a precursor ion mass selection window over time, in accordance with various embodiments. In FIG. 4, the x-axis is time or cycle number, the y-axis is product ion intensity, and the z-axis is m/z. From this three-dimensional plot, more information is obtained. For example, XIC peaks 410 and 420 both have the same shape and occur at the same time, or same retention time. However, XIC peaks 410 and 420 have different m/z values. This may mean that XIC peaks 410 and 420 are isotopic peaks or represent different product ions from the same precursor ion. Similarly, XIC peaks 430 and 440 have the same m/z value, but occur at different times. This may mean that XIC peaks 430 and 440 are the same product ion, but they are from two different precursor ions.

In various embodiments, the one or more compounds separated over time include peptides. As a result, the XIC for each precursor ion mass selection window can be filtered so that it includes only peptide XIC peaks. For example, XIC peaks with intensities below predetermined threshold intensity and non-isotopic XIC peaks can be excluded from each XIC.

2. Generate Binary Bit Matrix

In various embodiments, a binary bit matrix or array is formed that is used for each XIC of each precursor ion mass selection window. The rows of the binary bit matrix represent m/z or mass, for example. The columns of the binary bit matrix represent time or cycle number. The values of the binary bit matrix represent a peak of a product ion (1) or the absence of a peak of a product ion (0), for example.

In various embodiments, the binary bit matrix is used to identify peptides. The charge state of product ions of peptides can be determined through high-resolution mass spectrometry. This is done, for example, by determining the m/z difference between isotopic peaks. As a result, the mass or molecular weight of peptides can be determined from high-resolution mass spectrometry. In various embodiments, therefore, the rows of the binary bit matrix can represent product ion mass or molecular weight.

Figure 5:
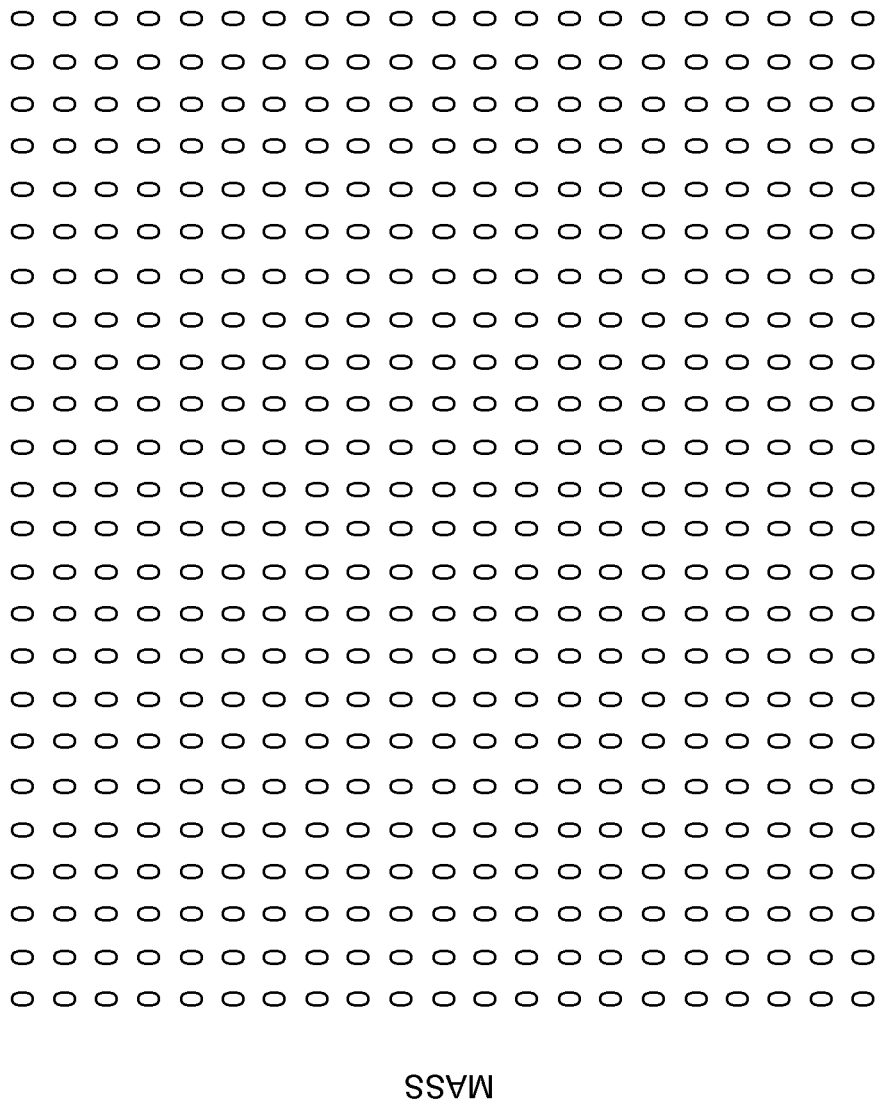
FIG. 5 is an exemplary diagram of a binary bit matrix, in accordance with various embodiments.

FIG. 5 is an exemplary diagram 500 of a binary bit matrix, in accordance with various embodiments. The rows of the binary bit matrix of FIG. 5 represent mass values, and the columns represent time or cycle values. Note that in various alternative embodiments the rows of the binary bit matrix can represent time or cycle values, and the columns can represent mass values. One of ordinary skill in the art can appreciate, however, that how the rows and columns of the binary bit matrix are assigned or indexed can affect how fast the matrix can be searched.

The binary bit matrix of FIG. 5 only shows 21 rows and 24 columns. Note that the binary bit matrix of FIG. 5 is only an example and the actual binary bit matrix used for identifying peptides can include on the order of millions of rows and thousands of columns. Note that the bit values are initially set to "0" or a value representing the absence of a product ion XIC peak.

In various embodiments, the mass dimension of the binary bit matrix is made to produce a constant parts per million (ppm) resolution across the mass range. In various embodiments, a constant ppm resolution in maintained in the mass dimension using a logarithmic scale.

$$\Delta = \frac{\ln(MZ_n) - \ln(MZ_0)}{N}, mz_i = MZ_0 e^{i\Delta},$$

$$i(mz) = \text{Round}\left(\frac{\ln(mz) - \ln(MZ_0)}{\Delta}\right),$$

$$\frac{mz_{i+1}}{mz_i} = \frac{MZ_0 e^{(i+1)\Delta}}{MZ_0 e^{i\Delta}} = e^{\Delta} - i \text{ invariant if we have predefined } ppm \text{ resolution } r,$$

then:

$$\Delta = \ln\left(1 + \frac{r}{1e6}\right), N = \frac{\ln(MZ_n) - \ln(MZ_0)}{\Delta},$$

where N—number of m/z points, $\Delta$ if constant log space delta, r—ppm resolution, mz—floating point value. For example, the number of mass points in the mass dimension is about 5 million for a mass range between 100 and 6000 daltons and a 1 ppm resolution.

In various embodiments, the mass dimension of the binary bit matrix is linear or constant. It is defined by the expected liquid chromatography (LC) resolution, for example.

3. Initialize Binary Bit Matrix for each XIC

In various embodiments, for each product ion XIC of each precursor mass selection window, the binary bit matrix is initialized or set. For example, LC-MS/MS features or product ion peaks are mapped onto the binary bit matrix. This is done separately for each precursor mass selection window. As a result, if there are K precursor mass selection windows, the binary bit matrix is separately mapped K times. The initialization can be done in a number of different ways to optimize performance. As one skilled in the art can appreciate, K different matrices can also be used. However, this is wasteful of processing memory.

In various embodiments, the binary bit matrix is initialized or the bits are set in transposed form to improve performance. In other words, the binary bit matrix is transposed before initialization so that rows represent time points and the columns represent product ion masses. This allows the binary bit matrix to be more efficiently searched or indexed by time.

During initialization, for each XIC or LC-MS/MS peak, the bits that are close to a peak time and mass are set to "1". In other words, a bit is set if the intensity of a product ion XIC peak at the mass and cycle time of the bit is within a predetermined peak intensity threshold. After initialization, the binary bit matrix is transposed again back to its "normal" state.

Figure 6:
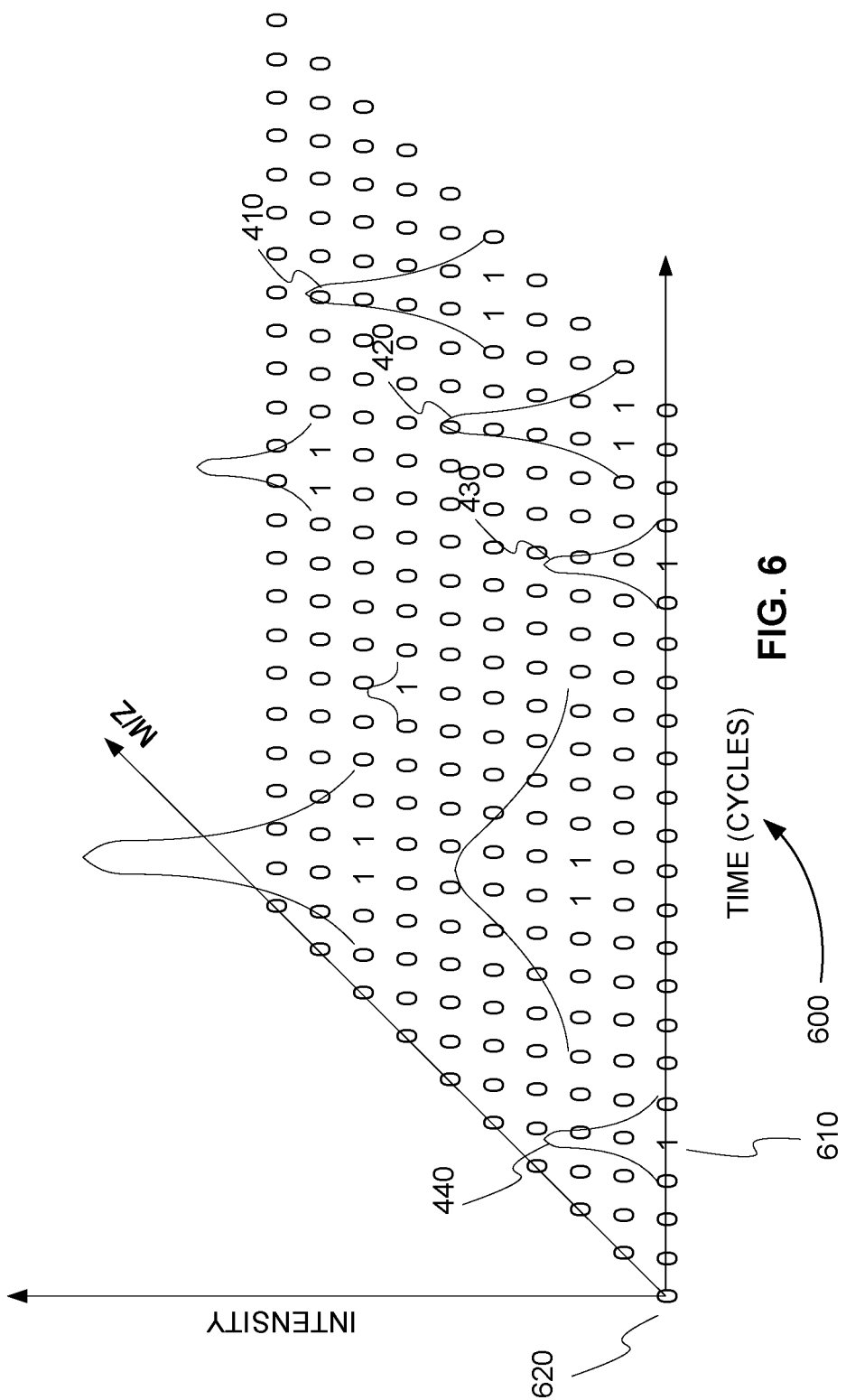
FIG. 6 is an exemplary diagram that shows how a binary bit matrix is initialized from the three-dimensional XICs obtained for each precursor ion mass selection window over time, in accordance with various embodiments.

FIG. 6 is an exemplary diagram 600 that shows how a binary bit matrix is initialized from the three-dimensional XICs obtained for each precursor ion mass selection window over time, in accordance with various embodiments. FIG. 6 depicts the same XIC as FIG. 4. However, the xz plane of FIG. 6 includes a binary bit matrix formed from the XIC peaks found in the XIC of FIG. 6.

As described above, a bit is set if the intensity of a product ion XIC at the mass and cycle time of the bit is within a predetermined peak intensity threshold. For example, at time 610 and m/z 620 of FIG. 6, XIC peak 440 is above a predetermined peak intensity threshold. As a result, the bit corresponding to time 610 and m/z 620 is set to "1." Note that bits are set for all of the XIC peaks shown in FIG. 6, including peaks 410, 420, and 430 in addition to peak 440. Also, note that in FIG. 6, one dimension of the matrix is m/z. As described above, for peptides this dimension can instead be mass or molecular weight.

4. Obtain Known Precursor Ion Stored Information

In order to identify known compounds in experimental tandem mass spectrometry data, stored information about the known compounds is used. This stored information can be stored in many different forms including, but not limited to, databases and flat files.

In various embodiments, stored information about known proteins or peptides is obtained from a FASTA file. The FASTA file is parsed. Theoretical peptides or theoretical peptide precursor ions are calculated from the parsed peptides or proteins by performing a computational digestion based on the same enzyme used in the actual mass spectrometry experiment.

5. Obtain Known Product Ion Information and Query Binary Bit Matrix

After obtaining theoretical precursor ion information from stored data, theoretical product ions are generated for each theoretical precursor ion. If the theoretical precursor ion is a peptide, for example, theoretical product ions are obtained by computationally fragmenting the theoretical peptide precursor ions. For example, the theoretical product ions are obtained by selecting the b and y fragments of the theoretical peptide precursor ions.

The theoretical precursor ions are matched to precursor ion mass selection windows of the tandem mass spectrometry data based on their m/z of mass values. Each theoretical precursor ion is then compared to the experimental XIC of its corresponding precursor ion mass selection window, by comparing the theoretical product ions of the theoretical precursor ion to the initialized binary bit matrix for that XIC.

In other words, for each theoretical precursor ion, the masses of its theoretical product ions are compared to the mass rows of the binary bit matrix initialized with the values from the corresponding product ion XIC. Each row of the binary bit matrix that corresponds in mass to a theoretical product ion and has at least one set bit, is copied from the binary bit matrix and stored as a bit mask for the theoretical precursor ion.

Figure 7:
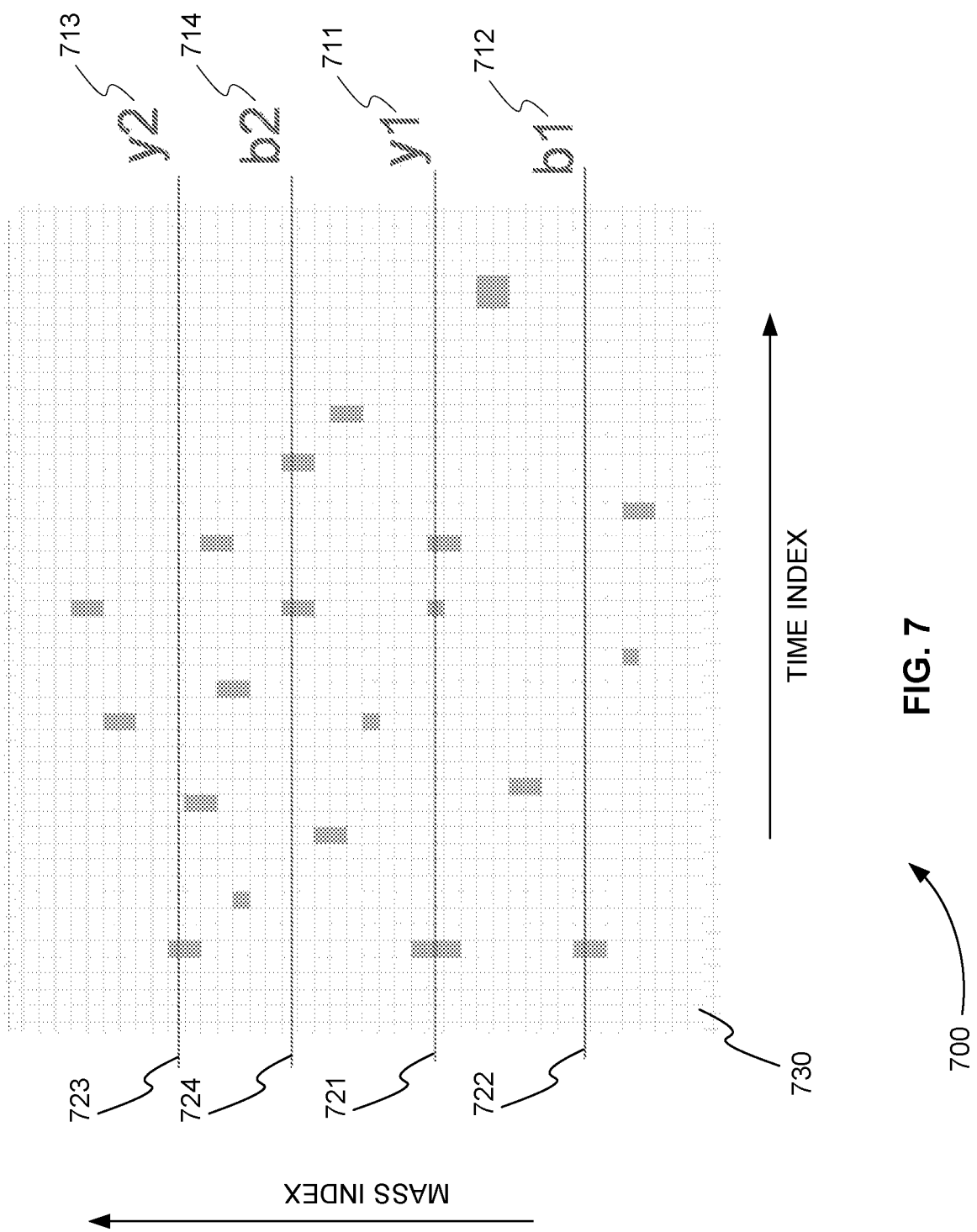
FIG. 7 is an exemplary diagram of a binary bit matrix showing how the theoretical product ions of a theoretical precursor ion are compared to the rows of a binary bit matrix that is initialized from the XIC of a precursor ion mass selection window, in accordance with various embodiments.

FIG. 7 is an exemplary diagram 700 of a binary bit matrix showing how the theoretical product ions of a theoretical precursor ion are compared to the rows of a binary bit matrix that is initialized from the XIC of a precursor ion mass selection window, in accordance with various embodiments. Four theoretical product ions 711, 712, 713, and 714 are generated for a theoretical peptide precursor ion, for example. Theoretical product ions 711 and 713 are y fragment ions of the theoretical peptide precursor ion, and theoretical product ions 712 and 714 are b fragment ions of the theoretical peptide precursor ion.

Each theoretical peptide precursor ion is matched to a precursor ion mass selection window of the mass spectrometry data by mass or m/z value. Binary bit matrix 730 is initialized based on the intensity values of the XIC of the matching precursor ion mass selection window. Set bits of binary bit matrix 730 are shown as shaded blocks. Binary bit matrix 730 includes, for example, r mass rows and c time columns. Binary bit matrix 730, therefore, can be stored in r×c/8 bytes of processing memory.

The masses of theoretical product ions 711-714 are compared to the mass rows of initialized binary bit matrix 730. Mass rows 721-724 are found to correspond to theoretical product ions 711-714, respectively. Each of mass rows 721-724 also includes a set bit. As a result, each of mass rows 721-724 is copied from the binary bit matrix and stored as a bit mask for the theoretical peptide precursor ion.

6. Arrange Bit Masks into Submatrix

For each theoretical precursor ion, its bit masks are arranged into a submatrix. In this submatrix, the rows are the bit masks of the theoretical precursor ion. In other words, the rows are the copied rows of the binary bit matrix that have a mass value that matches a mass of a theoretical product ion of the theoretical precursor ion and that have at least one set bit. The submatrix, therefore, typically has many fewer rows than the binary bit matrix. The submatrix has the same number of columns as the binary bit matrix.

Figure 8:
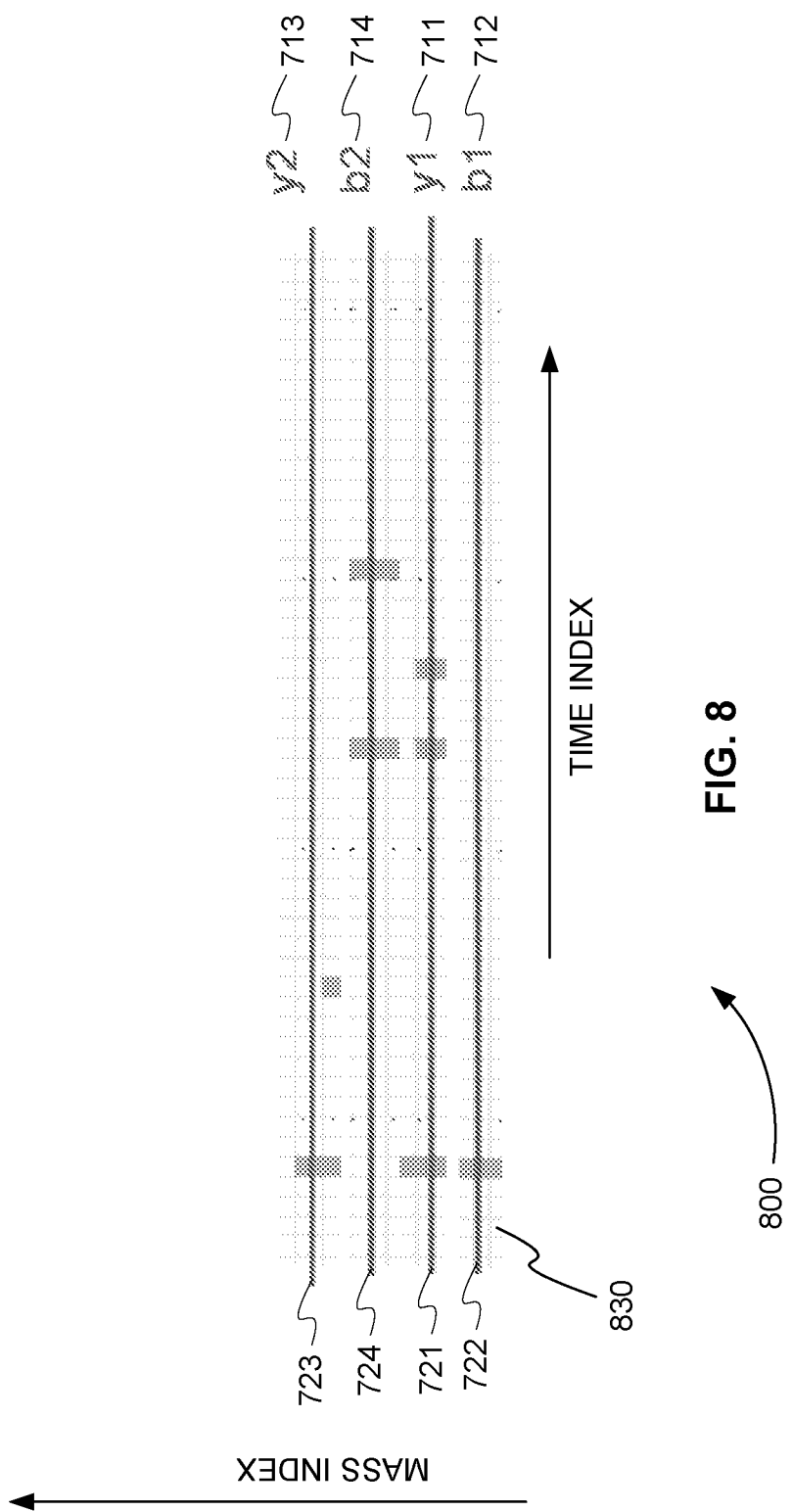
FIG. 8 is an exemplary diagram of a submatrix of a theoretical peptide precursor ion that is arranged from the bit masks of a binary bit matrix that correspond to theoretical product ions of the theoretical peptide precursor ion, in accordance with various embodiments.

FIG. 8 is an exemplary diagram 800 of a submatrix of a theoretical peptide precursor ion that is arranged from the bit masks of a binary bit matrix that correspond to theoretical product ions of the theoretical peptide precursor ion, in accordance with various embodiments. Submatrix 830 includes four mass rows 721-724. These four mass rows 721-724 correspond, respectively, to theoretical product ions 711-714 of a theoretical peptide precursor ion. Submatrix 830 includes the same number of columns as binary bit matrix 730 of FIG. 7.

Submatrix 830 includes, for example, 4 mass rows and c time columns. Submatrix 830, therefore, can be stored in 4×c/8 bytes of processing memory.

7. Count Set Bits of Submatrix at Each Time Point

Each submatrix of each theoretical precursor ion is used to score the theoretical precursor ion. Each time point of each submatrix is indexed, and the bits at the time point are counted, providing a count or score for each time point. In various embodiments, in order to more efficiently index each time point of each submatrix, each submatrix is transposed before indexing.

Figure 9:
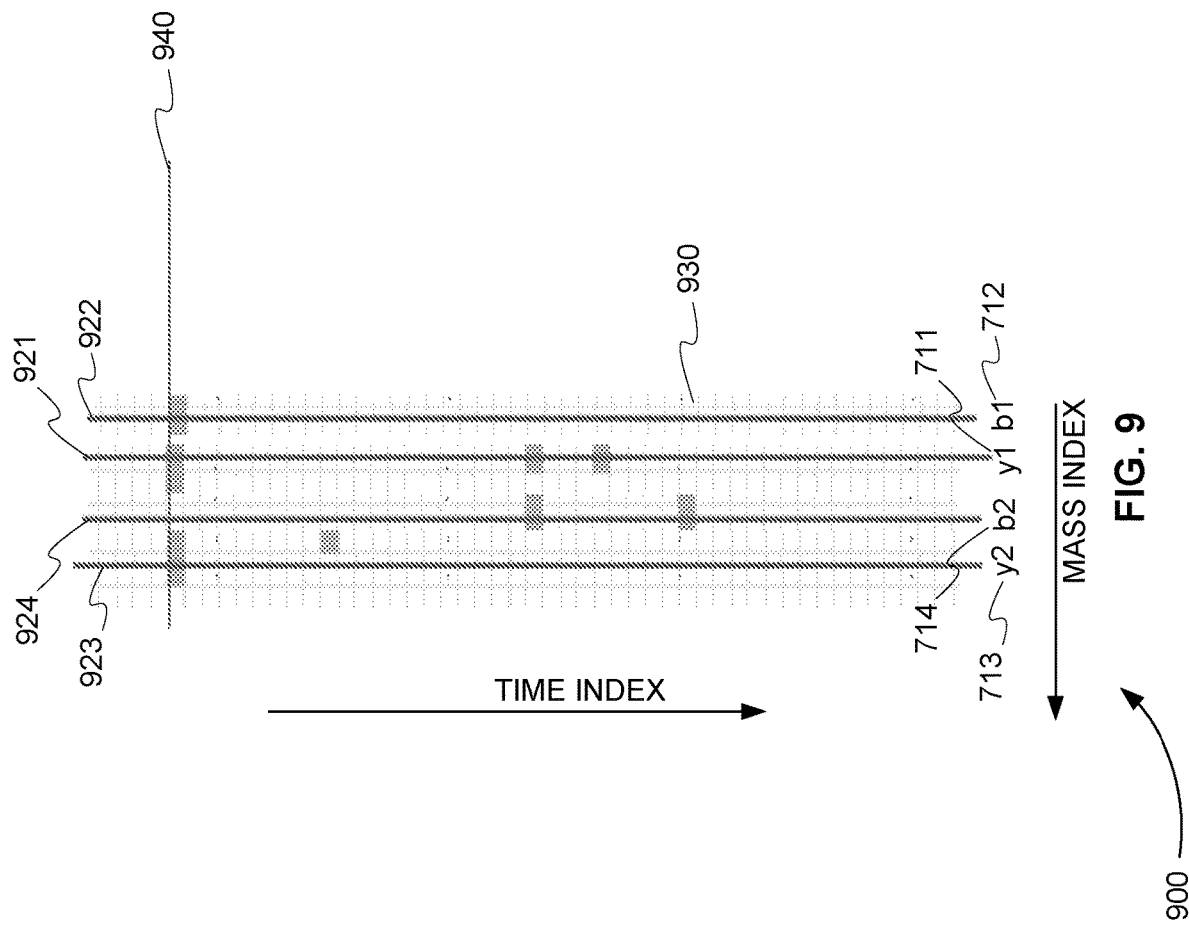
FIG. 9 is an exemplary diagram of a transposed submatrix of a theoretical peptide precursor ion showing how the bits at each time point are counted, in accordance with various embodiments.

FIG. 9 is an exemplary diagram 900 of a transposed submatrix of a theoretical peptide precursor ion showing how the bits at each time point are counted, in accordance with various embodiments. Transposed submatrix 930 includes four mass columns 921-924. These four mass columns 921-924 correspond, respectively, to theoretical product ions 711-714 of a theoretical peptide precursor ion. Transposed submatrix 930 includes the same number of time rows and the number of time columns in binary bit matrix 730 of FIG. 7. Transposed submatrix 930 of FIG. 9 is the transposed form of submatrix 830 of FIG. 8.

Transposed submatrix 930 is used to score its corresponding theoretical peptide. Each time point or row of transposed submatrix 930 is selected and indexed. The bits in each row are then counted. For example, the bits of row 940 are counted to provide a count or score for the time point represented by row 940.

Typically, a theoretical peptide precursor ion has less than 64 theoretical fragments or product ions. Therefore, at each time point, less than 64 bits need to be counted. Current processors, or central processing units (CPUs), can count 64 or 128 bits using a single instruction. In various embodiments, the bits in each row of each transposed submatrix of each theoretical peptide precursor ion are counted using a single instruction, CPU cycle, or clock cycle of a processor.

As describe above, the mass spectrometry industry was previously unable to obtain computationally efficient methods of comparing product ions of theoretical peptides with measured product ion spectra that each include large numbers of different product ions. As just described, the use of a binary bit matrix and more particularly submatrices of the binary bit matrix allows each time point of experimental mass spectrometry data to be compared to a theoretical peptide in a single instruction of a processor. As a result, various embodiments described herein can significantly improve the performance of a processor in identifying compounds in a sample analyzed using a DIA method, such as SWATH acquisition.

8. Calculate Probability of Getting Set Bits at Each Time Point Randomly

In various embodiments, for each theoretical precursor ion, a probability value is calculated. This probability value is the probability that the scores or counts calculated at each time point of the corresponding submatrix were obtained randomly. The probability value is then used to determine if the theoretical precursor ion is identified in the experimental sample. For example, if the probability value indicates that there is a low probability that the scores or counts calculated at each time point of the corresponding submatrix were obtained randomly, it is likely that the theoretical precursor ion is in the experimental sample.

System for Identifying Compounds using a Binary Bit Matrix

Figure 10:
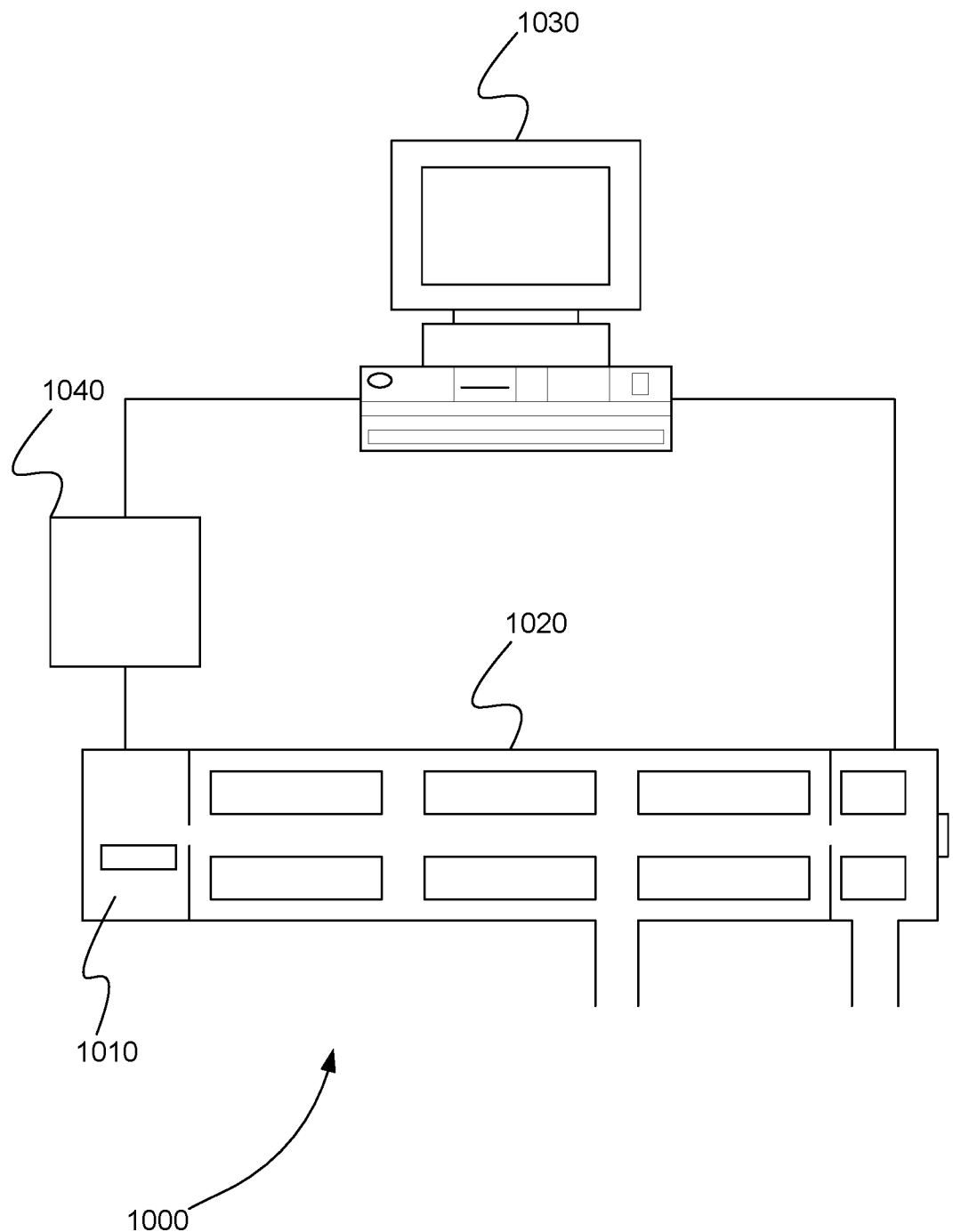
FIG. 10 is a schematic diagram of a system for representing product ion XICs obtained from a tandem mass spectrometry DIA experiment as a binary bit matrix and using the binary bit matrix to identify compounds by comparing the binary bit matrix to stored information about known compounds, in accordance with various embodiments.

FIG. 10 is a schematic diagram of a system 1000 for representing product ion XICs obtained from a tandem mass spectrometry DIA experiment as a binary bit matrix and using the binary bit matrix to identify compounds by comparing the binary bit matrix to stored information about known compounds, in accordance with various embodiments. System 1000 includes ion source 1010, tandem mass spectrometer 1020, and processor 1030. In various embodiments, system 1000 can also include sample introduction device 1040.

Sample introduction device 1040 can provide a sample to ion source 710 using one of a variety of techniques. These techniques include, but are not limited to, gas chromatography (GC), liquid chromatography (LC), capillary electrophoresis (CE), or flow injection analysis (FIA). Sample introduction device 1040 introduces one or more compounds of a sample over time.

Ion source 1010 can be part of tandem mass spectrometer 1020, or can be a separate device. Ion source 1010 is configured to receive the one or more compounds from sample introduction device 1040 and ionize the one or more compounds, producing an ion beam of precursor ions.

Tandem mass spectrometer 1020 can include, for example, one or more physical mass filters and one or more physical mass analyzers. A mass analyzer of tandem mass spectrometer 1020 can include, but is not limited to, a time-of-flight (TOF), quadrupole, an ion trap, a linear ion trap, an orbitrap, or a Fourier transform mass analyzer.

Tandem mass spectrometer 1020 is configured to receive the ion beam of precursor ions that divides an m/z range of the ion beam into two or more precursor ion mass selection windows and selects and fragments the two or more precursor ion mass selection windows during each cycle of a plurality of cycles, producing a plurality of product ion spectra for each precursor ion mass selection window of the two or more precursor ion mass selection windows.

Processor 1030 can be, but is not limited to, a computer, microprocessor, or any device capable of sending and receiving control signals and data from tandem mass spectrometer 1020 and processing data. Processor 1030 can be, for example, computer system 100 of FIG. 1. In various embodiments, processor 1030 is in communication with tandem mass spectrometer 1020 and sample introduction device 1040.

Processor 1030 receives a plurality of product ion spectra for each precursor ion mass selection window of the two or more precursor ion mass selection windows. Processor 1030 calculates a product ion XIC for each precursor ion mass selection window of the two or more precursor ion mass selection windows from the plurality of product ion spectra for each precursor ion mass selection window, producing two or more product ion XICs.

Processor 1030 generates a two-dimensional binary bit matrix to represent each product ion XIC of the two or more product ion XICs. A first dimension of the binary bit matrix represents a mass of a product ion XIC. A second dimension of the binary bit matrix represents a cycle time of the product ion XIC. Each element of the binary bit matrix is a binary value that represents whether or not an intensity of a product ion XIC at each mass and cycle time is within a predetermined peak intensity threshold.

For each XIC of the two or more product ion XICs, processor 1030 separately initializes the binary bit matrix with binary values calculated from each XIC. Processor 1030 compares the initialized binary bit matrix with stored information about known compounds to identify known compounds of each XIC.

In various embodiments, the one or more compounds and the known compounds comprise peptides.

In various embodiments, the binary value "1" represents that an intensity of a product ion XIC at each mass and cycle time is within a predetermined peak intensity threshold. The binary value "0" represents that an intensity of a product ion XIC at each mass and cycle time is not within a predetermined peak intensity threshold.

In various embodiments, a first dimension comprises a row of the binary bit matrix and the second dimension of the binary bit matrix comprises a column of the binary bit matrix.

In various embodiments, values of the first dimension are calculated to preserve a constant parts per million (ppm) resolution across a mass range of the first dimension.

In various embodiments, a distance between the values of the first dimension, Δ, are calculated on a logarithmic scale. For example, $$\Delta = \frac{\ln(M_n) - \ln(M_0)}{N},$$

where N is number of mass points across the mass range and M is the mass at each mass point.

In various embodiments, processor 1030 further transposes the binary bit matrix before initializing the binary bit matrix for the each XIC. After the binary bit matrix is transposed, the first dimension comprises a column of the binary bit matrix and the second dimension of the binary bit matrix comprises a row of the binary bit matrix. Processor 1030 transposes the binary bit matrix again after initializing the binary bit matrix for the each XIC.

In various embodiments, processor 1030, for each XIC of the two or more product ion XICs, compares the initialized binary bit matrix with stored information about known compounds to identify known compounds of the each XIC by performing a series of steps for each known compound of the stored information that has a mass to charge ratio (m/z) within an m/z range of the precursor ion mass selection window of the each XIC. First, processor 1030, generates generating a list of product ions. Processor 1030 generates a submatrix from the binary bit matrix by copying from the binary bit matrix to the submatrix each row that corresponds in mass to a product ion of the list. Processor 1030 transposes the submatrix so that the rows of the submatrix represent cycle time values and the columns represent mass values. Processor 1030 calculates the number of set bits in each row, producing a cycle time score for each cycle time and a plurality of cycle time scores. Processor 1030 calculates a probability of getting the plurality of cycle time scores at random. Finally, processor 1030 identifies each known compound as a compound of each XIC based on the probability.

In various embodiments, processor 1030 calculates the number of set bits in each row in one clock cycle of the processor.

In various embodiments, the stored information about known compounds includes a FASTA formatted file of peptides. Processor 1030 generates a list of product ions by parsing the file for peptides. Processor 1030 performs a computational digestion of the parsed peptides yielding a plurality of theoretical precursor ions. Processor 1030 fragments each of the plurality of theoretical precursor ions to produce a list of product ions.

In various embodiments, fragmenting each of the plurality of theoretical precursor ions to produce a list of product ions comprises determining b and y fragment ions of each of the plurality of theoretical precursor ions.

Method for Identifying Compounds using a Binary Bit Matrix

Figure 11:
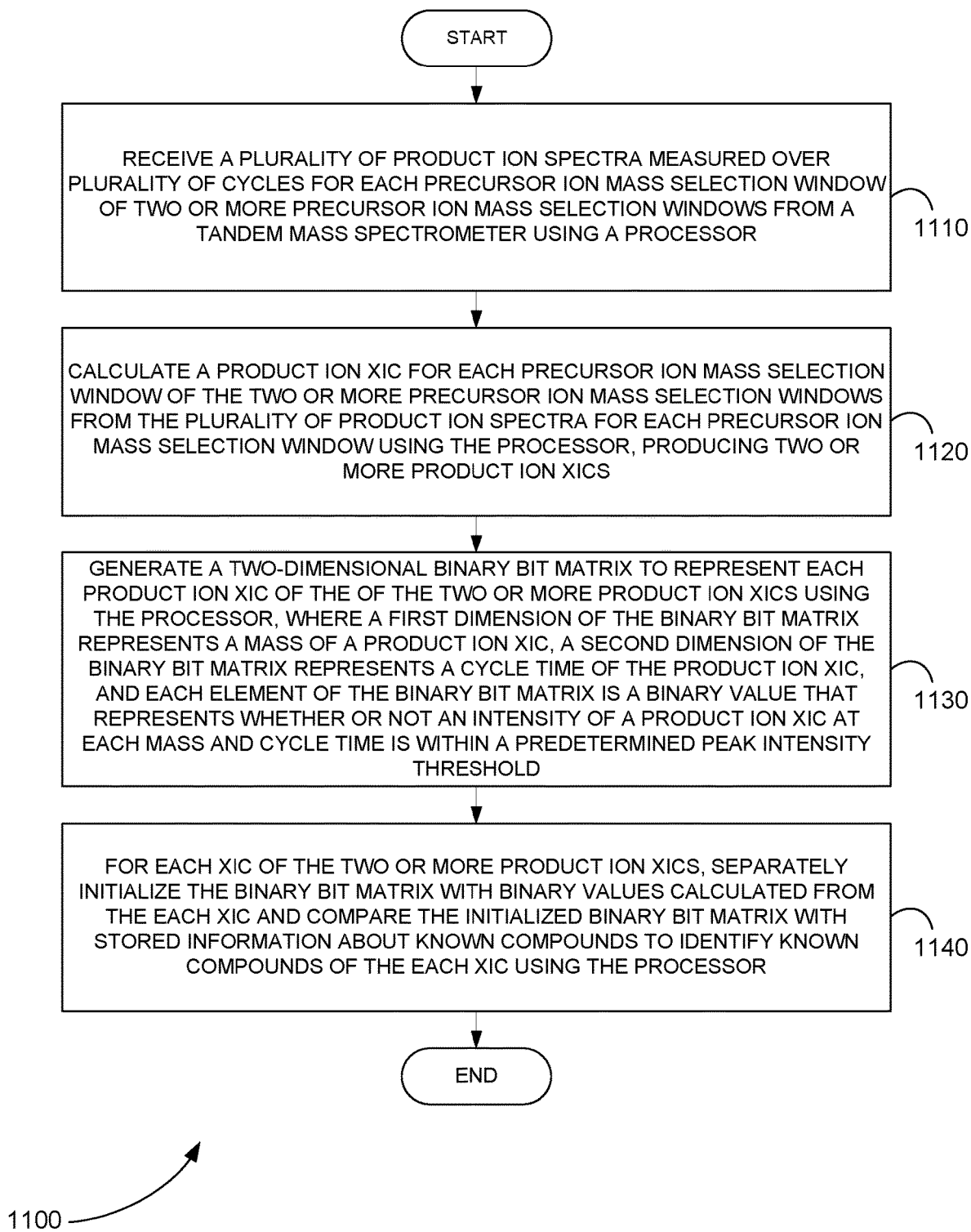
FIG. 11 is a flowchart showing a method for representing product ion XICs obtained from a tandem mass spectrometry DIA experiment as a binary bit matrix and using the binary bit matrix to identify compounds by comparing the binary bit matrix to stored information about known compounds, in accordance with various embodiments.

FIG. 11 is a flowchart showing a method 1100 for representing product ion XICs obtained from a tandem mass spectrometry DIA experiment as a binary bit matrix and using the binary bit matrix to identify compounds by comparing the binary bit matrix to stored information about known compounds, in accordance with various embodiments.

In step 1110 of method 1100, a plurality of product ion spectra measured over a plurality of cycles for each precursor ion mass selection window of two or more precursor ion mass selection windows is received from a tandem mass spectrometer using a processor. The plurality of product ion spectra are produced by the tandem mass spectrometer by dividing an m/z range of an ion beam into two or more precursor ion mass selection windows and selecting and fragmenting the two or more precursor ion mass selection windows during each cycle of the plurality of cycles. The ion beam is produced by an ion source that ionizes one or more compounds of a sample. The one or more compounds are produced by a sample introduction device that introduces one or more compounds of a sample to the ion source over time.

In step 1120, a product ion XIC is calculated for each precursor ion mass selection window of the two or more precursor ion mass selection windows from the plurality of product ion spectra for each precursor ion mass selection window using the processor. Two or more product ion XICs are produced.

In step 1130, a two-dimensional binary bit matrix is generated to represent each product ion XIC of the two or more product ion XICs using the processor. A first dimension of the binary bit matrix represents a mass of a product ion XIC. A second dimension of the binary bit matrix represents a cycle time of the product ion XIC. Each element of the binary bit matrix is a binary value that represents whether or not an intensity of a product ion XIC at each mass and cycle time is within a predetermined peak intensity threshold.

In step 1140, for each XIC of the two or more product ion XICs, the binary bit matrix is separately initialized with binary values calculated from the each XIC and the initialized binary bit matrix is compared with stored information about known compounds to identify known compounds of the each XIC using the processor.

Computer Program Product for Identifying Compounds using a Binary Bit Matrix

In various embodiments, computer program products include a tangible computer-readable storage medium whose contents include a program with instructions being executed on a processor so as to perform a method for representing product ion XICs obtained from a tandem mass spectrometry DIA experiment as a binary bit matrix and using the binary bit matrix to identify compounds by comparing the binary bit matrix to stored information about known compounds. This method is performed by a system that includes one or more distinct software modules.

Figure 12:
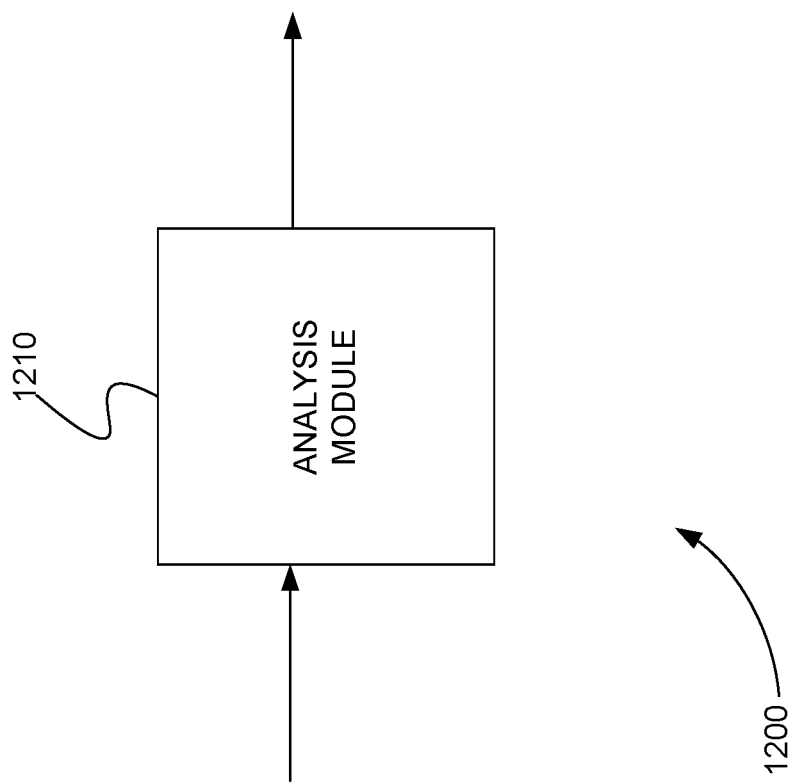
FIG. 12 is a schematic diagram of a system that includes one or more distinct software modules that performs a method for representing product ion XICs obtained from a tandem mass spectrometry DIA experiment as a binary bit matrix and using the binary bit matrix to identify compounds by comparing the binary bit matrix to stored information about known compounds, in accordance with various embodiments.

FIG. 12 is a schematic diagram of a system 1200 that includes one or more distinct software modules that performs a method for representing product ion XICs obtained from a tandem mass spectrometry DIA experiment as a binary bit matrix and using the binary bit matrix to identify compounds by comparing the binary bit matrix to stored information about known compounds, in accordance with various embodiments. System 1200 includes analysis module 1210.

Analysis module 1210 receives receiving a plurality of product ion spectra for each precursor ion mass selection window of two or more precursor ion mass selection windows from a tandem mass spectrometer. The plurality of product ion spectra is produced by the tandem mass spectrometer by dividing m/z range of an ion beam into two or more precursor ion mass selection windows and selecting and fragmenting the two or more precursor ion mass selection windows during each cycle of a plurality of cycles. The ion beam is produced by an ion source that ionizes one or more compounds of a sample. The one or more compounds are produced by a sample introduction device that introduces one or more compounds of a sample to the ion source over time.

Analysis module 1210 calculates a product ion XIC for each precursor ion mass selection window of the two or more precursor ion mass selection windows from the plurality of product ion spectra for each precursor ion mass selection window, producing two or more product ion XICs. Analysis module 1210 generates a two-dimensional binary bit matrix to represent each product ion XIC of the two or more product ion XICs. A first dimension of the binary bit matrix represents a mass of a product ion XIC. A second dimension of the binary bit matrix represents a cycle time of the product ion XIC. Each element of the binary bit matrix is a binary value that represents whether or not an intensity of a product ion XIC at each mass and cycle time is within a predetermined peak intensity threshold.

For each XIC of the two or more product ion XICs, analysis module 1210 separately initializes the binary bit matrix with binary values calculated from the each XIC. Analysis module 1210 then compares the initialized binary bit matrix with stored information about known compounds to identify known compounds of the each XIC.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for representing product ion extracted ion chromatograms (XICs) obtained from a tandem mass spectrometry data independent acquisition (DIA) experiment as a binary bit matrix and using the binary bit matrix to identify compounds by comparing the binary bit matrix to stored information about known compounds, comprising:
a sample introduction device that introduces one or more compounds of a sample over time;
an ion source configured to receive the one or more compounds from the sample introduction device and ionize the one or more compounds, producing an ion beam of precursor ions;
a tandem mass spectrometer configured to receive the ion beam of precursor ions that divides a mass-to-charge ratio (m/z) range of the ion beam into two or more precursor ion mass selection windows and selects and fragments the two or more precursor ion mass selection windows during each cycle of a plurality of cycles, producing a plurality of product ion spectra for each precursor ion mass selection window of the two or more precursor ion mass selection windows; and
a processor in communication with the tandem mass spectrometer that
receives the plurality of product ion spectra for each precursor ion mass selection window of the two or more precursor ion mass selection windows,
calculates a product ion XIC for each precursor ion mass selection window of the two or more precursor ion mass selection windows from the plurality of product ion spectra for each precursor ion mass selection window, producing two or more product ion XICs,
generates a two-dimensional binary bit matrix to represent each product ion XIC of the two or more product ion XICs, wherein a first dimension of the binary bit matrix represents a mass of a product ion XIC, a second dimension of the binary bit matrix represents a cycle time of the product ion XIC, and each element of the binary bit matrix is a binary value that represents whether or not an intensity of a product ion XIC at each mass and cycle time is within a predetermined peak intensity threshold, and
for each XIC of the two or more product ion XICs, separately initializes the binary bit matrix with binary values calculated from the each XIC and compares the initialized binary bit matrix with stored information about known compounds to identify known compounds of the each XIC.

2. The system of claim 1, wherein the sample introduction device comprises a liquid chromatography device.

3. The system of claim 1, wherein the one or more compounds and the known compounds comprise peptides.

4. The system of claim 1, wherein a binary value that represents that an intensity of a product ion XIC at each mass and cycle time is within a predetermined peak intensity threshold comprises 1, and a binary value that represents that an intensity of a product ion XIC at each mass and cycle time is not within a predetermined peak intensity threshold comprises 0.

5. The system of claim 4, wherein the first dimension comprises a row of the binary bit matrix and the second dimension of the binary bit matrix comprises a column of the binary bit matrix.

6. The system of claim 1, wherein values of the first dimension are calculated to preserve a constant parts per million (ppm) resolution across a mass range of the first dimension.

7. The system of claim 6, wherein a distance between the values of the first dimension, Δ, are calculated on a logarithmic scale.

8. The system of claim 6, wherein $$\Delta = \frac{\ln(M_n) - \ln(M_0)}{N},$$

where N is number of mass points across the mass range, and $M_i$ is the mass at each mass point, and i's are values range from 0, 1, 2, 3, . . . , n, where n is an integer.

9. The system of claim 5, wherein the processor further transposes the binary bit matrix before initializing the binary bit matrix for the each XIC so that the first dimension comprises a column of the binary bit matrix and the second dimension of the binary bit matrix comprises a row of the binary bit matrix and transposes the binary bit matrix again after initializing the binary bit matrix for the each XIC.

10. The system of claim 5, wherein the processor, for each XIC of the two or more product ion XICs, compares the initialized binary bit matrix with stored information about known compounds to identify known compounds of the each XIC by,
for each known compound of the stored information that has a mass to charge ratio (m/z) within an m/z range of the precursor ion mass selection window of the each XIC,
generating a list of product ions,
generating a submatrix from the binary bit matrix by copying from the binary bit matrix to the submatrix each row that corresponds in mass to a product ion of the list,
transposing the submatrix so that the rows of the submatrix represent cycle time values and the columns represent mass values,
calculating the number of set bits in each row, producing a cycle time score for each cycle time and a plurality of cycle time scores,
calculating a probability of getting the plurality of cycle time scores at random, and identifying the each known compound as a compound of the each XIC based on the probability.

11. The system of claim 10, wherein the processor calculates the number of set bits in each row in one clock cycle of the processor.

12. The system of claim 10, wherein the stored information about known compounds comprises a FASTA formatted file of peptides, and the processor generates a list of product ions by parsing the file for peptides, performing a computational digestion of the parsed peptides yielding a plurality of theoretical precursor ions, and fragmenting each of the plurality of theoretical precursor ions to produce a list of product ions.

13. The system of claim 12, wherein fragmenting each of the plurality of theoretical precursor ions to produce a list of product ions comprises determining b and y fragment ions of each of the plurality of theoretical precursor ions.

14. A method for representing product ion extracted ion chromatograms (XICs) obtained from a tandem mass spectrometry data independent acquisition (DIA) experiment as a binary bit matrix and using the binary bit matrix to identify compounds by comparing the binary bit matrix to stored information about known compounds, comprising:
receiving a plurality of product ion spectra for each precursor ion mass selection window of two or more precursor ion mass selection windows from a tandem mass spectrometer using a processor,
wherein the plurality of product ion spectra is produced by the tandem mass spectrometer by dividing a mass-to-charge ratio (m/z) range of an ion beam into two or more precursor ion mass selection windows and selecting and fragmenting the two or more precursor ion mass selection windows during each cycle of a plurality of cycles,
  wherein the ion beam is produced by an ion source that ionizes one or more compounds of a sample, and
  wherein the one or more compounds are produced by a sample introduction device that introduces one or more compounds of a sample to the ion source over time;
calculating a product ion XIC for each precursor ion mass selection window of the two or more precursor ion mass selection windows from the plurality of product ion spectra for each precursor ion mass selection window using the processor, producing two or more product ion XICs;
generating a two-dimensional binary bit matrix to represent each product ion XIC of the two or more product ion XICs using the processor, wherein a first dimension of the binary bit matrix represents a mass of a product ion XIC, a second dimension of the binary bit matrix represents a cycle time of the product ion XIC, and each element of the binary bit matrix is a binary value that represents whether or not an intensity of a product ion XIC at each mass and cycle time is within a predetermined peak intensity threshold; and
for each XIC of the two or more product ion XICs, separately initializing the binary bit matrix with binary values calculated from the each XIC and comparing the initialized binary bit matrix with stored information about known compounds to identify known compounds of the each XIC using the processor.

15. A computer program product, comprising a non-transitory and tangible computer-readable storage medium whose contents include a program with instructions being executed on a processor so as to perform a method for representing product ion extracted ion chromatograms (XICs) obtained from a tandem mass spectrometry data independent acquisition (DIA) experiment as a binary bit matrix and using the binary bit matrix to identify compounds by comparing the binary bit matrix to stored information about known compounds, comprising:

providing a system, wherein the system comprises one or more distinct software modules, and wherein the distinct software modules comprise an analysis module;
receiving a plurality of product ion spectra for each precursor ion mass selection window of two or more precursor ion mass selection windows from a tandem mass spectrometer using the analysis module,
  wherein the plurality of product ion spectra is produced by the tandem mass spectrometer by dividing a mass-to-charge ratio (m/z) range of an ion beam into two or more precursor ion mass selection windows and selecting and fragmenting the two or more precursor ion mass selection windows during each cycle of a plurality of cycles,
  wherein the ion beam is produced by an ion source that ionizes one or more compounds of a sample, and
  wherein the one or more compounds are produced by a sample introduction device that introduces one or more compounds of a sample to the ion source over time;
calculating a product ion XIC for each precursor ion mass selection window of the two or more precursor ion mass selection windows from the plurality of product ion spectra for each precursor ion mass selection window using the analysis module, producing two or more product ion XICs;
generating a two-dimensional binary bit matrix to represent each product ion XIC of the two or more product ion XICs using the analysis module, wherein a first dimension of the binary bit matrix represents a mass of a product ion XIC, a second dimension of the binary bit matrix represents a cycle time of the product ion XIC, and each element of the binary bit matrix is a binary value that represents whether or not an intensity of a product ion XIC at each mass and cycle time is within a predetermined peak intensity threshold; and
for each XIC of the two or more product ion XICs, separately initializing the binary bit matrix with binary values calculated from the each XIC and comparing the initialized binary bit matrix with stored information about known compounds to identify known compounds of the each XIC using the analysis module.

* * * * *